United States Patent [19]
Inga et al.

[11] Patent Number: 5,384,643
[45] Date of Patent: Jan. 24, 1995

[54] IMAGE TRANSMISSION SYSTEM WITH PATTERNED DATA COMPRESSION

[75] Inventors: Jorge J. Inga; Thomas V. Saliga, both of Tampa, Fla.

[73] Assignee: Automate Medical Access Corporation, Tampa, Fla.

[21] Appl. No.: 206,525

[22] Filed: Mar. 4, 1994

Related U.S. Application Data

[62] Division of Ser. No. 915,298, Jul. 20, 1992, Pat. No. 5,321,520.

[51] Int. Cl.$^6$ .............................................. H04N 1/41
[52] U.S. Cl. .................................... 358/403; 358/426; 382/56; 364/413.19
[58] Field of Search ............... 358/403, 426, 428, 429, 358/430, 432, 433, 261.3, 261.2, 261.1, 443, 447, 448, 458, 455, 453, 450, 540, 530, 532, 538, 540; 382/56; 395/114; 348/390, 404, 420, 415; 364/413.19, 413.22, 413.13

[56] References Cited

U.S. PATENT DOCUMENTS

| | | | |
|---|---|---|---|
| 4,606,069 | 8/1986 | Johnsen | 382/56 |
| 4,783,841 | 11/1988 | Crayson | 382/56 |
| 4,811,112 | 3/1989 | Rutledge | 358/261.2 |
| 5,014,198 | 5/1991 | Umemura | 382/56 |
| 5,293,230 | 3/1994 | Colin | 348/415 |
| 5,303,313 | 4/1994 | Mark et al. | 382/56 |
| 5,305,103 | 4/1994 | Golin | 348/415 |

*Primary Examiner*—Scott A. Rogers
*Attorney, Agent, or Firm*—David Kiewit

[57] ABSTRACT

A storage, retrieval, and transmission system is configured to provide fast, efficient telecommunication access to digitized images (e.g., medical diagnostic X-ray images) to multiple requesting subscribers. Image data are downloaded, via the telephone lines, to a remote display terminal in an optimal fashion that employs a two-dimensional patterned data compression scheme. The data compression methods include a "Hex-Pac" compression in which one first generates regions comprising a plurality of two dimensional, non-overlapping, symmetrically disposed super pixels that are collectively representative of an image. Each of these regions is subsequently compared with a plurality of fictitious patterns, each of which has a dark region, a light region and a predetermined point of origin, in order to determine which of the patterns most closely correlates with the selected region.

22 Claims, 9 Drawing Sheets

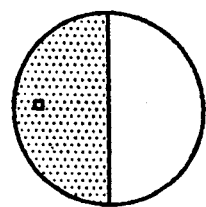
*Fig. 14-A*
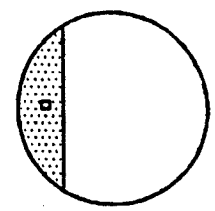
*Fig. 14-B*
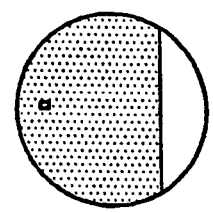
*Fig. 14-C*
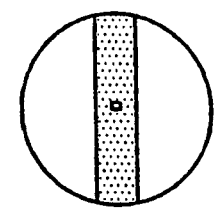
*Fig. 14-D*
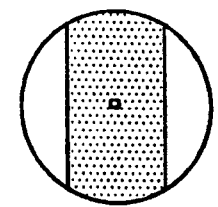
*Fig. 14-E*
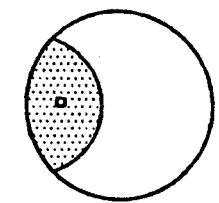
*Fig. 14-F*
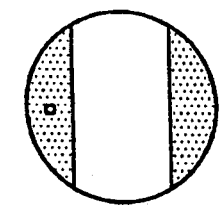
*Fig. 14-G*
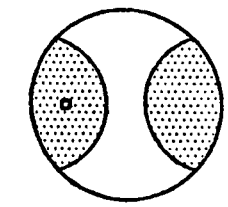
*Fig. 14-H*

IMAGE TRANSMISSION SYSTEM WITH PATTERNED DATA COMPRESSION

This application is a division of U.S. patent application Ser. No. 07/915,298 which was filed Jul. 20, 1992 now U.S. Pat. No. 5,321,520

BACKGROUND OF THE INVENTION

Storage and retrieval systems for medical image data such as X-ray films, CAT scans, angiograms, tomograms and MRI are commonly antiquated. For example, when image films are used in the operating room, the physician must display these photo films on a light box.

Moreover, due to the diffuse responsibilities of multiple attending physicians and treatment sites, image data for patients with complex conditions is often lost, or at best, difficult to find when needed. Hospitals maintain large "file rooms" to store bulky patient image data films. In a complex situation in which several folders are needed, a file's weight can build up to 7 kg. It has proven time consuming to obtain image data from file rooms due to administrative backlogs, to lack of specialized filing personnel and to misfiling.

Typically, the physician examines the patient in his office after the radiographical studies have been made in a hospital or diagnostic facility. These films and the information contained therein are often unavailable at the time of the examination. Thus, there is a need for remote access to these image data for rapid patient assessment and therapy recommendation.

U.S. Pat. No. 4,603,254 teaches a stimulable phosphor sheet carrying a radiation image stored therein scanned with stimulating rays. The light emitted from the stimulable phosphor sheet in proportion to the radiation energy stored therein is detected and converted into an electric signal converted to a digital signal. Digital data is created to reproduce the radiation image for use in diagnosis and storage.

U.S. Pat. No. 4,764,870 describes a system for transferring medical diagnostic information from the diagnostic site to remote stations. An internal analog video signal from imaging diagnostic equipment such as a CAT scanner or MRI equipment, is converted to an analog video signal of different, preferably standard, format that is stored and transmitted in the reformatted image information to the remote terminal. The received signal is stored, decoded and applied in appropriate analog video form to an associated CRT display for reproduction of the diagnostic images.

U.S. Pat. No. 5,005,126 shows a system for transferring medical diagnostic information from the diagnostic site to remote stations similar to that found in U.S. Pat. No. 4,764,870.

U.S. Pat. No. 5,019,975 teaches a method for constructing a data base in a medical image filing system comprising the steps or recording information indicating the time at which each medical image is recorded and a rank of importance for each medical image as image retrieval signal data for image signals corresponding to each medical image; recording the number of times the image signals corresponding to each medical image have been retrieved as image retrieval signal data and incrementing the number each time the image signals are retrieved; and when the data base is full of image retrieval signal data, deleting the image retrieval signal data corresponding to the image signals of the medical image in which at least (1) the time at which the medical image was recorded earlier than a predetermined time and (2) the rank of importance of the medical image is lower than a predetermined value.

U.S. Pat. No. 4,611,247 describes a radiation image reproducing apparatus to read a radiation image from a first recording medium as a visible image. Input devices of the apparatus enter data which are associated with a method of exposing an object to a radiation and object's exposed part. In response to the input data, a processing condition determining unit determines conditions optimum for a gradation processing and a spatial frequency processing. A processor system is provided for reading the radiation image stored in the first recording medium and processing the radiation image on the basis of conditions which the processing condition determining unit determines in response to the input data associated with the radiation image.

U.S. Pat. No. 4,750,137 discloses a method and a computer program for performing the method for optimizing signals being exchanged between a host unit and an addressable-buffer peripheral device. The program optimizes an outgoing signal from the host unit by (1) creating an updated-state map representing the state of the peripheral device buffer expected to exist after processing by the peripheral device of the outgoing signal, (2) performing an exclusive-or (XOR) operation using the updated-state map and a present-state map representing the existing state of the buffer, and (3) constructing and transmitting a substitute outgoing signal which represents only changes to the buffer, and in which all premodified field flags are turned off. Position-dependent characters, such as attribute bytes, are translated into nondata characters prior to incorporation into a map, and are retranslated into their original form for use in the substitute signal.

U.S. Pat. No. 4,858,129 teaches an X-ray CT apparatus in which a plurality of dynamic tomographic images obtained by repeatedly photographing a region of interest of a subject under examination are stored in an image memory for subsequent display on a display device. A processing device extracts data of pixels along a certain line common to all of the tomographic images and stores the pixel data in the image memory, in the order of photographing time of the tomographic images, thus forming a time sequence image formed of picked-up pixels. The processing device reduces a tomographic image and the time sequence image and rearranges the reduced images in one frame area of the image memory for simultaneous display thereof on the display device.

U.S. Pat. No. 5,021,770 discloses an image display system having a plurality of CRT display screens. The system is of the type in which a number of images of specific portions of a patient having a specific identification code are selected from among a multitude of X-ray image taken by a plurality of shooting methods, and when the regions or interest are specific, a plurality of appropriate images are further selected using the previously stored amplitude values for the regions and shooting methods and displayed on the plurality of CRT display screens. In order that the segments to be inspected can be pointed to on the screen on which the image of the patient is displayed, a memory is provided which is adapted to previously store codes corresponding to the specific image of the patient and to specify the respective regions of the image in such a manner that they correspond to the pixels positions of the image.

U.S. Pat. No. 4,879,665 teaches a medical picture filing system composed of a picture data memory device, a picture data input-output device for inputting/outputting the picture data, a retrieving device for storing the picture data into the memory device and extracting it therefrom on the basis of retrieving data, a retrieving data input device for inputting the retrieving data into the retrieving device, a retrieving data storing device for storing the retrieving data, the retrieving data being classified by block of information obtained in one-time examination. When medical pictures are filed, retrieving data collected for each examination is utilized for reducing the amount of retrieving data, while when reproduced, retrieval is carried out for each one-time examination thereby shortening the time required for retrieval.

In light of recent advances in computer data basing, digitization and compression of image data, image enhancement algorithms and cost effective computer technology, the means for improved storage and retrieval of vital patient image data is now possible.

Such system should include the following major features:

1) means to more compactly store and more efficiently retrieve image data and automatically identify the data by patient name, image type, date and the like;

2) means for physicians to quickly and remotely access particular patient image data at the medical facility even if archived at several different locations;

3) means to prevent loss of vital image data due to ordinary human handling and misplacement errors;

4) means to quickly and affordably access image data from the physician's office;

5) means to enhance the medical images by both contrast enhancement and zooming for improved diagnostics and/or surgical guidance; and 6) means to quickly and conveniently access image data and display on a large screen in the operating room with any desired enhancement or expansion.

As described more fully hereinafter, the present invention provides means to accomplish these goals. The system uses both general purpose system elements well known to those practiced in electronic arts and specific elements having significant novelty.

SUMMARY OF THE INVENTION

The present invention relates to an automated high definition/resolution image storage, retrieval and transmission system capable for storing, transmitting and displaying medical diagnostic quality images for use with medical X-ray films or the like.

The system comprises means to process the image data from patient imaging to physician usage. The major or significant processing stages are described hereinafter. Specifically, the major steps in the image data flow include:

PATIENT RADIOGRAPHY: The patient's body is imaged and a film is exposed as in an X-ray room, MRI or CAT scan lab.

FILM PREPARATION: The film(s) is developed to create a visible image with OCR readable patient identification information superimposed thereon.

FILM INTERPRETATION: Commonly, a radiologist drafts an opinion letter for the film(s). This document preferrably includes an optical character reader, or OCR, readable patient identification label or standard marking area.

IMAGE SCANNING & DIGITIZING SUBSYSTEM: A scanner subsystem digitizes each patient image film and/or document on a high resolution scanner. This digitized data is transmitted by a local high speed data link to a separate or remote master storage unit. Patient identification information is read from a standard format on each file by OCR techniques and efficiently stored with the digitized image data. Enhanced scanner resolution and gray scale requirements are provided. Further, to reduce data rate requirements, data compaction or compression is accomplished within the scanner subsystem.

To back-up possible data link down time or scanner down time, the scanner subsystem may include a CD-ROM data storage drive so that image data may continue to be digitized. The CD-ROM disk may then be manually delivered to the file room unit for subsequent use.

In an optional embodiment, the digitized data of one or two images may be written to a compact semi-conductor memory card "RAM Cards". This form of data storage may be used to send selected images for special purposes such as when the image data is needed in another city for second opinion purposes.

At this point in the image data flow, there is a split in which the original film data is stored as a "master" in a file room and the image disk is made available for active "on-line" use in an image storage and retrieval subsystem.

FILM FILING: The patient image films may be placed in the industry standard 14 by 17 inch brown paper folders and placed on conventional filing shelves. However, it is preferred that older films be tagged and stored off-site to reduce the current excessive bulk of films in many hospital file rooms. The system would now make this practical since the original films would seldom need to be accessed.

In the preferred embodiment of the system, the patient may have his entire image data collected and written to one or more of the storage CD-ROM disks for archiving at the hospital.

IMAGE STORAGE AND RETRIEVAL SUBSYSTEM: This subsystem is a remotely controllable, automatically accessable image data subsystem to store and automatically retrieve, on-demand, the compressed digital information contained on the CD-ROM disks.

The image storage and retrieval subsystem has a high-speed data link connection to the scanning and digitizing subsystem and has a write drive recording mechanism which is dedicated to receiving the data from the scanning and digitizing subsystem. This CD-ROM write drive can operate without interrupting remote access operations.

Remote access may be made to the image storage and retrieval subsystem by a variety of telecommunication links. Access will be granted only if a valid user code has been presented. By means of several read-only CD disk drives and electronic buffering, virtually simultaneous access can be granted to several or more users.

As explained more fully hereinafter, the medical image disk will contain relatively huge quantities of data making it impractical to send over conventional data communication links without very efficient data compression technology. While there are variety of data compression techniques available, none are well tailored to this application. Thus, novel compression means are in the remote telecommunication access subsystem.

TELECOMMUNICATION SUBSYSTEM: Occasionally circumstances may warrant manually making an extra copy of the patient's image files to be physically delivered to an authorized requester. However, for the system to fulfill broad service to the health care industry it must be able to efficiently telecommunicate image files to remote locations both cost effectively and within a reasonable time interval.

A novel medical facsimile technology is in the preferred embodiment which works interactively with a remote requester to send only what is needed at acceptable resolutions, and the presented image is progressively updated as the communications connection is maintained until the resolution limits of the user display are reached, after which time, other images are either sent or further enhanced.

The specific technical means for accomplishing this uses the following novel technologies: a) guided image selection & transmission (GIST); b) progressive image enhancement (PIE); c) display compatible resolution (DCR); d) hexagonal pattern classification compression (HexPac) and e) run length coding (RLC), RLC is well known to those skilled in the arts.

It appears practical to send immediately useful patient data in less than one minute over a phone line (9600 baud) whereas it take many hours by conventional coding and transmission means. When wide-band telecommunications as satellite, fiber optic, micro-wave links becomes more generally available at affordable prices, then the more complex data compression techniques described here will be less important, but until that time, these types of techniques are believed essential to overall system success.

This combination of technologies to efficiently compress the image data and transmit remotely comprises the telecommunication access subsystem. In practice, these technologies may be implemented for the most part with available computer modules although several special signal processor boards are needed.

REMOTE DISPLAY TERMINAL: The quality of the image available to the user is limited or determined by the receiving presentation terminal or monitor. Two specific presentation terminal types are envisioned in the preferred embodiment of the system, a modified personal computer terminal for use in a physician's office, hospital nurses' station and the like, and a large screen presentation terminal with remote controlled interaction primarily for operating room use.

Both terminals have means to show the available patient directory of images, and means to select an image, enhancement and zoom on selected areas. Image enhancement has heretofore been impractical for film based images and thus much subtle but important pathological information has been largely lost. This is especially true of X-ray data. The ability to enhance subtle contrasted tissues areas is considered to be an important feature and benefit of the system.

An optional high-resolution printer (300 dpi or better) permits the physician to print out selected images. This will be especially valuable when the physician expands and enhances selected critical image areas since a cost effective printer would otherwise not have adequate gray scale or pixel resolution to give diagnostically useful output.

Each terminal consists of a standard high performance personal computer with one or more data source interfaces such as RAM card, CD-ROM disk or data modem, a decompression graphics interface circuit and graphics display. The large screen presentation terminal has a large screen display for easy viewing for a surgeon who may be ten or more feet distant. The large screen presentation terminal also has an optional remote control so that an attending technician or nurse can scroll images, enhance and zoom, at the surgeon's request.

A keynote of each terminal design is a very simple user interface based upon a limited selection menu and obviously pointed-to graphical icons.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which:

FIGS. 14-A through 14-H depict the predetermined set of orthogonal gray level patterns.

Similar reference characters refer to similar parts throughout the several views of the drawings.

DETAILED DESCRIPTION OF THE PREFERRED EMBODIMENT

Figure 1:
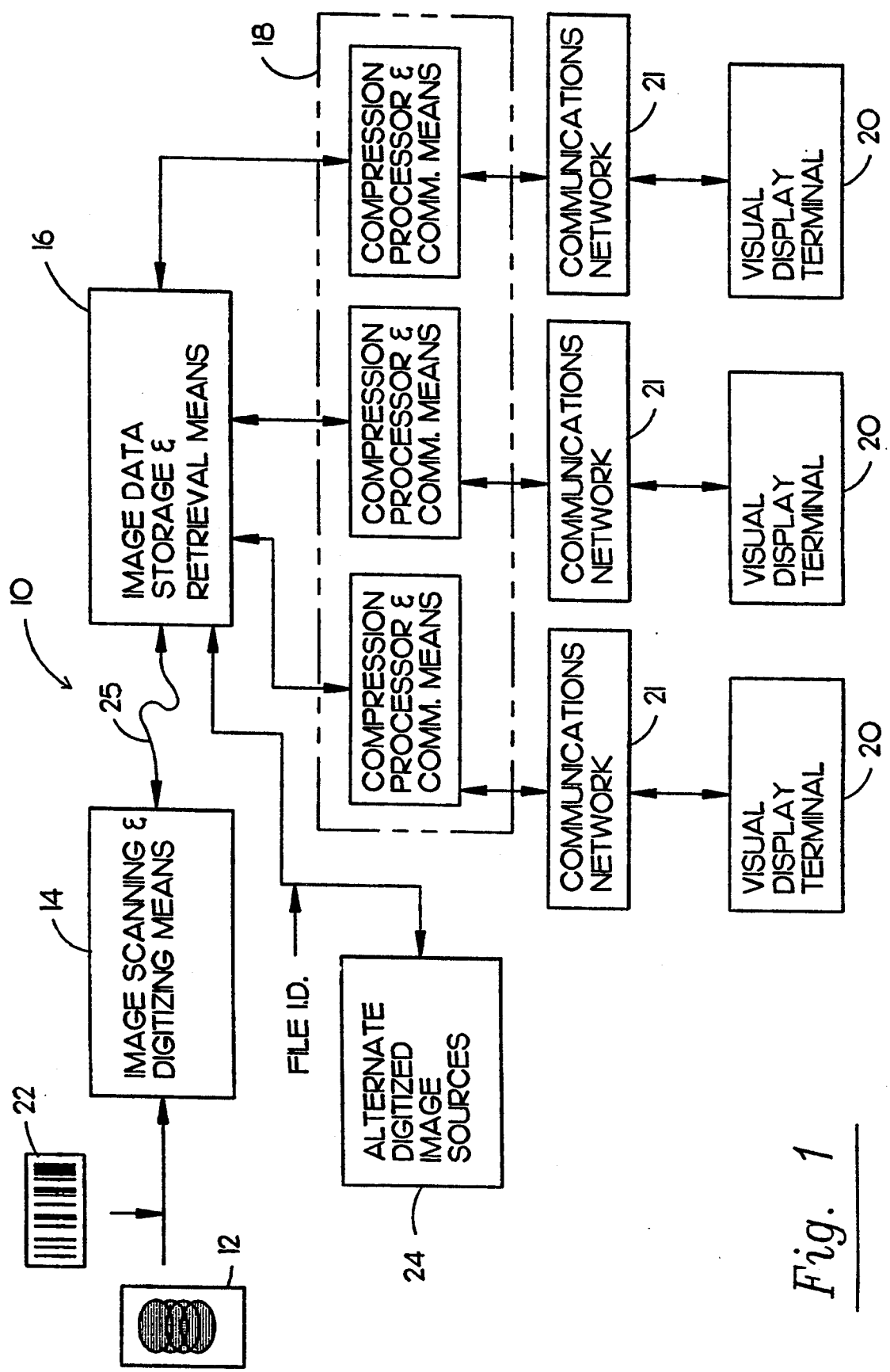
FIG. 1 is a functional block diagram of the entire system of the present invention.

As shown in FIG. 1, the present invention relates to an automated high definition/resolution image storage, retrieval and transmission system generally indicated as 10 for use with medical X-ray film 12 or other documents to provide simultaneous automated access to a common data base by a plurality of remote subscribers upon request from the remote subscribers.

The automated high definition/resolution image storage, retrieval and transmission system 10 comprises an image scanning and digitizing means 14 to transform the visual image from the medical X-ray film 12 or other documents into digital data, an image data storage and retrieval means 16 to store and selectively transfer digital data upon request, a telecommunication means 18 to selectively receive digital data from the image data storage and retrieval means 16 for transmission to one of a plurality of remote visual display terminals each indicated as 20 upon request from the respective remote visual display terminal 20 through a corresponding communications network 21 such as a telephone line, satellite link, cable network or local area network such as Ethernet or an ISDN service for conversion to a visual image for display at the remote requesting site.

To improve automation and tracking, a machine readable indicia or label 22 containing key patient information may be used in association with the medical X-ray film 12. As shown, the machine readable indicia or label 22 is affixed to the medical X-ray film 12 prior to scanning by the image scanning and digitizing means 14 to provide file access and identification. Furthermore, digital data from alternate digitized image sources collectively indicated as 24 and file identification may be fed to the image data storage and retrieval means 16 for storage and retrieval.

Figure 2:
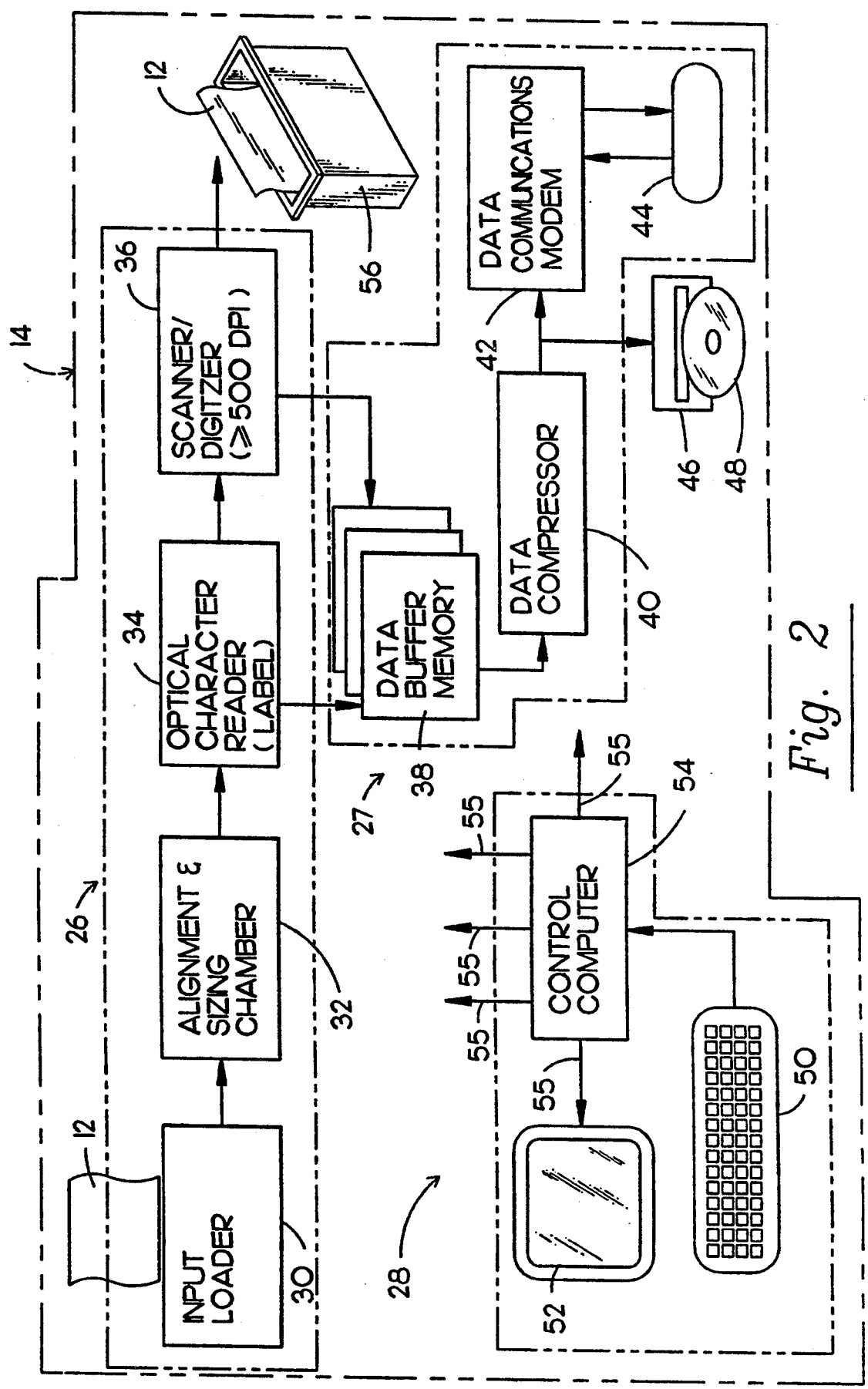
FIG. 2 is a functional block diagram of the image scanning and digitizing means.

FIG. 2 is a functional block diagram of the image scanning and digitizing means 14 capable of converting the visual image from the medical X-ray film 12 to digitized image data for transmission to the image data storage and retrieval means 16 over a bi-directional high speed data link 25. Specifically, the image scanning and digitizing means 14 comprises a film loading and scanning section and a data compression and transmission section generally indicated as 26 and 27 respectively and a display and control section generally indicated as 28. The film loading and scanning section 26 comprises a film input loader 30, alignment and sizing chamber 32, optical character reader 34 and film scanner/digitizer 36 capable of at least 500 dots per inch resolution 36; while, the data compression and transmission section 27 comprises a data buffer memory 38, low-loss data compression means 40, local data modem 42 and transmission connector 44 to operatively couple the image scanning and digitizing means 14 to the image data storage and retrieval means 16. The low-loss data compressor 40 is also operatively coupled to a compact disk data storage drive 46 capable of writing or storing compressed digitized patient image data on a compact disk 48. The display and control section 28 comprises a keyboard/control console 50, display terminal 52 and control computer 54 which is operatively coupled to the other components of the image scanning and digitizing means 14 through a plurality of conductors each indicated as 55. A film collector tray 56 may be disposed adjacent the film scanner/digitizer 36 to receive the medical X-ray film 12 therefrom following processing.

To reduce the approximately 238 Megapixels required to digitize a 14 inch by 17 inch, medical X-ray film 12 with 700 dots or pixels per inch with a two byte level to a manageable size without significant information loss, a linear gray level prediction, modified run-length code generating logic circuitry is embodied within the low-loss data compression means 40 to dynamically compress the digitized data before storage or recording. The image data is compressed with acceptable diagnostic resolution loss. The low-loss data compression means 40 measures the "local" slope of the pixel gray level and continues to compare that estimated gray level for up to an entire scan line until a pixel region is reached which differs from the linear estimate by more than a predetermined amount. The data actually sent for that region consists of the slope of the line, actual level at the origin of the slope line and the number of pixels comprising that region. The circuitry will discard linear gray level slope differences of the original film which can be reliably determined to be noise or image "artifacts". A sudden one pixel (if at 1000 dots per inch) dramatic change in gray level could be rejected as dust or film noise for example. The compressed data is a trade-off between complexity, speed and minimum data loss to reduce the total data quantity stored by a factor of approximately three. Thus, about 80 Megapixels of data may still have to be stored per 14 inch by 17 inch film image.

In the preferred embodiment, the bi-directional high speed communications link 25 transmits the low-loss compressed digitized data from the developing lab room to the hospital file room where the image data storage and retrieval means 16 will transfer and store the patient and image data in a new patient file on a compact disk 48.

Two way communications between the image scanning and digitizing means 14 and the image data storage and retrieval means 16 minimizes data loss by insuring that a compact disk 48 be available to receive and store data. Moreover, the compact disk data storage drive 46 with re-writable ROM technology can record data even if communications with the image data storage and retrieval means 16 is disrupted. Thus the image scanning and digitizing means 14 can automatically start writing data to the compact disk data storage drive 46 as soon as a image data storage and retrieval means 16 fault is sensed. The display and control section 28 informs the operator of the system status.

In operation, the film lab technician may stack one or more medical X-ray films 12 onto the input loader 30 as shown in FIG. 2. A "read" button is depressed on the keyboard/control console 50 and each film 12 is thereafter fed in automatically, digitized and transmitted to the image data storage and retrieval means 16 located in the file room. As the reading of each film 12 is completed, the film 12 is deposited into the film collector tray 56. System status, number-of-films read logging and so forth are shown on the display terminal 52.

Initially, the image scanning and digitizing means 14 positions the film 12 in the alignment and sizing chamber 32 on a precision carrying platen for subsequent optical scanning. This platen contains optical sensors to sense the exact film size so only the useful image area is digitized. Once the film 12 is secured onto the movable platen, the film 12 is passed through the optical character reader 34 and then to the film scanner/digitizer 36.

The patient data and image identification is first recorded onto the remote CD-ROM file directory in the image data storage and retrieval means 16 from the OCR "pass" and then the compressed scanned image data is sequentially written to a compact disk 48 by a CD write drive for storage with the CD library storage of the image data storage and retrieval means 16 as described more fully hereinafter as the film 12 slowly passes through the film scanner/digitizer 36.

Specifically, the film scanner/digitizer 36 converts the image to a digital representation of preferably at least a 700 dot per inch resolution. This digital data is temporarily stored in the data buffer memory 38 where the patient data from the optical character reader 34 and corresponding digitized image data from the file scanner/digitizer 36 are properly formatted for subsequent compression and transmission to the image data storage and retrieval means 16. The stored data is then accessed by and compressed by the data compression means 40 as previously described and transmitted through the local data modem 42 and transmission connector 44 to the image data storage and retrieval means 16 or a compact disk data storage drive 46. The display and control section 28 permits the X-ray lab staff to monitor system status, report quantity of documents and films processed and allow for scheduling local recording of image data on compact disks 48.

Figure 3:
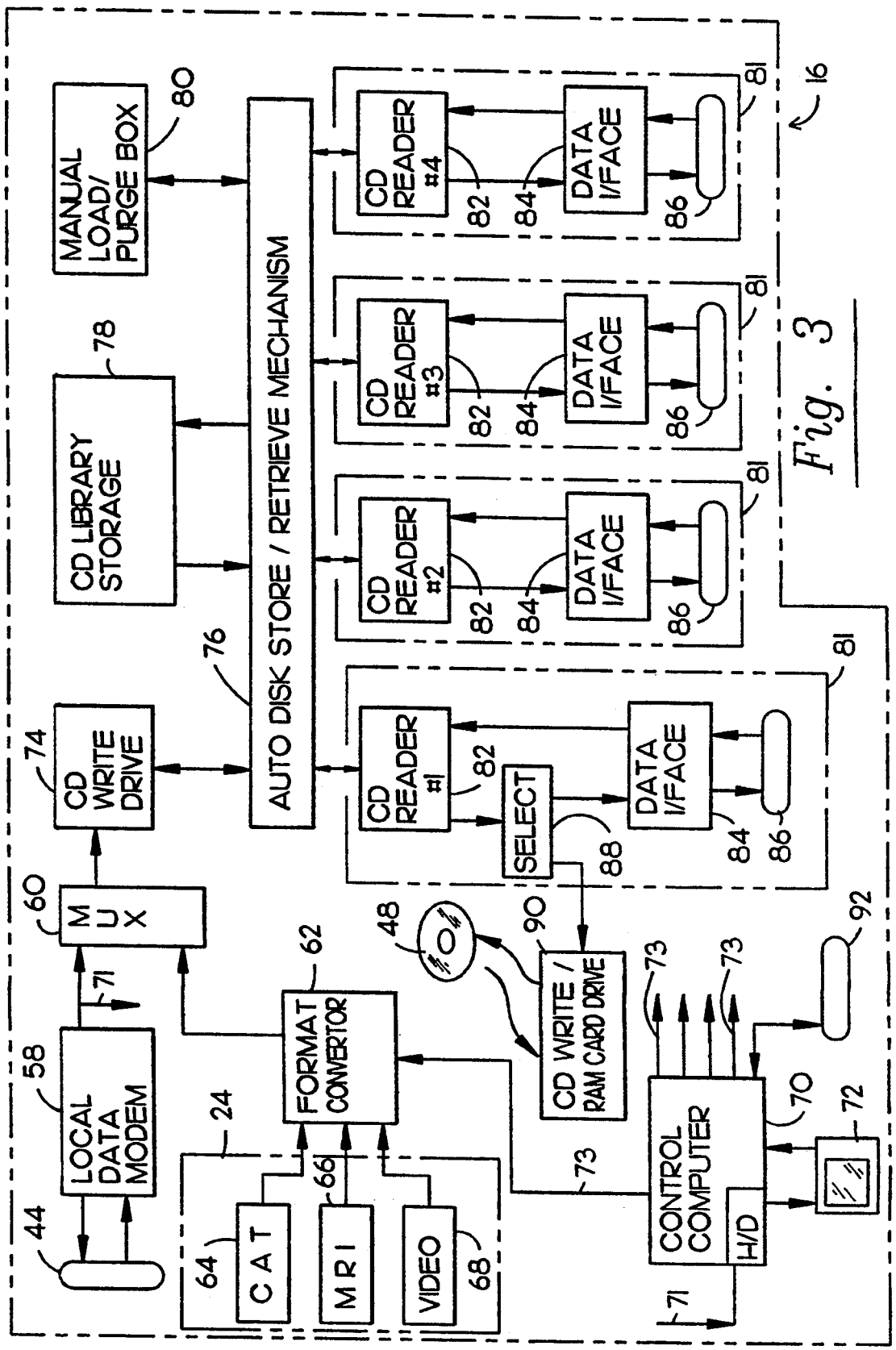
FIG. 3 is a functional block diagram of the image data storage and retrieval means.
Figure 4:
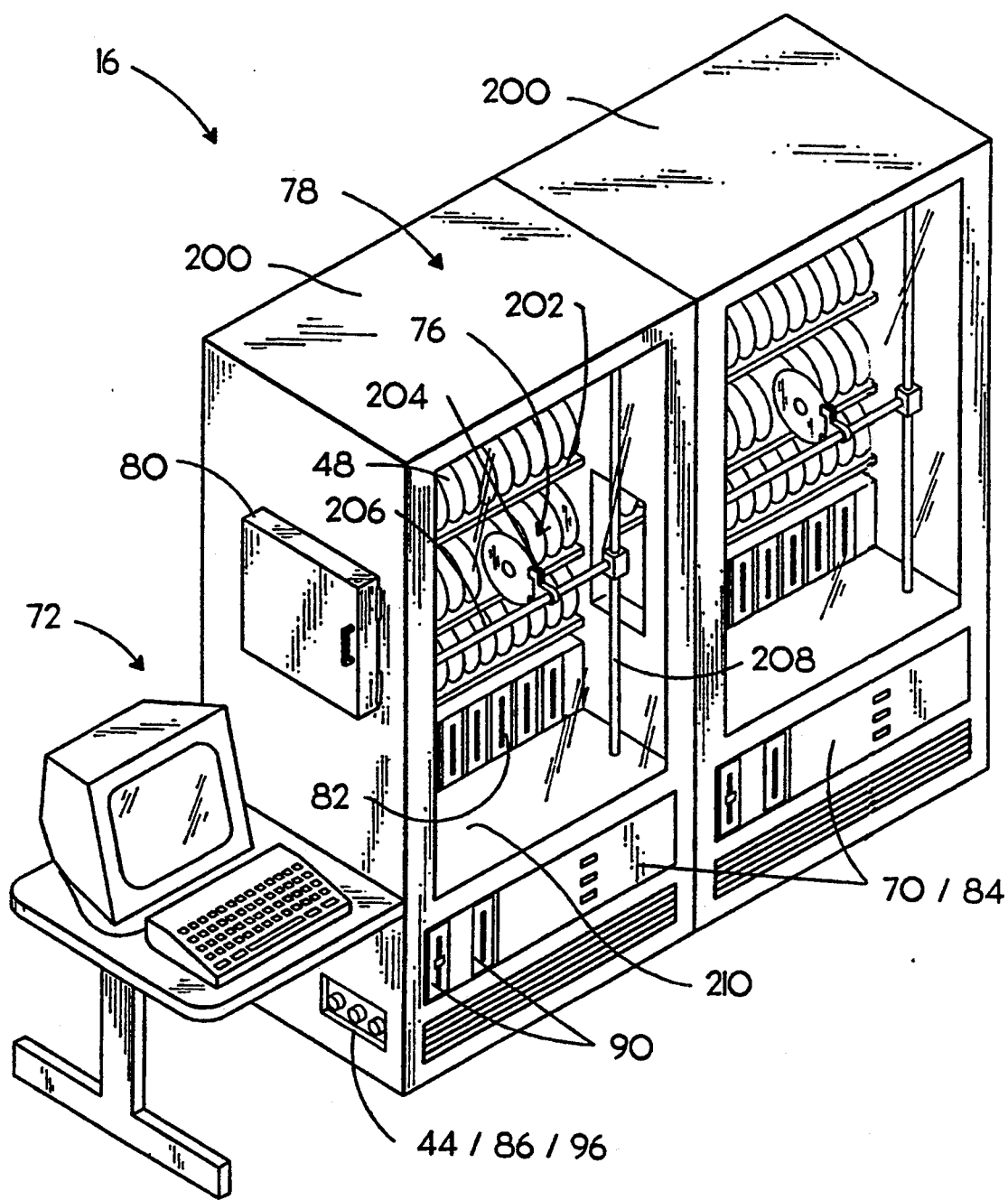
FIG. 4 is a perspective view of the image data storage and retrieval means.

FIGS. 3 and 4 show the image data storage and retrieval means 16 to receive and store the low-loss compressed digitized patient information and image data from the image scanning and digitizing means 14 and to selectively transmit the stored low-loss compressed digitized patient information and image data to one or more of the remote visual display terminal(s) 20 through corresponding telecommunication means 18 and corresponding communications network(s) 21 upon request from one or more of the remote display terminal(s) 20.

The image data and retrieval means 16 is essentially a central data storage library for medical subscribers to remotely access and visually display patient data and information.

As described hereinafter, the image data storage and retrieval means 16 is robotically automated to minimize hospital staff requirements. At any given time, it is estimated that a typical hospital may have several hundred active patients with requirements for physician access to corresponding image files. An active patient may require one to three compact disks 48. Thus, the image data storage and retrieval means 16 should have sufficient means to store and retrieve at least 500 compact disks 48.

Further, to minimize personnel requirements, the image data storage and retrieval means 16 has a semiautomatic log-in mechanism for updating the compact disk inventory and an automatic mechanism for retrieving and reading the compact disks 48 remotely via communication link interfaces similar to juke box playback mechanisms. Except for the occasional loading of new empty compact disks 48 and removal of inactive compact disks 48, the operation of the image data storage and retrieval means 16 is fully automatic, permitting authorized access at any time.

As described more fully hereinafter, several playback drives with electronic buffering are incorporated so that essentially simultaneous access can be provided to several remote requesting users. An optional duplicating CD write drive and RAM-Card drive permits additional copies to be made locally upon demand for either back-up or other use. The image data storage and retrieval means 16 has an operator's console/desk arrangement for file maintenance and duplicating control by the hospital file room clerk. Control software is a simple menu selection design so that relatively unskilled personnel can maintain the central data storage library or image data bank.

As shown in the functional block diagram of FIG. 3, the image data storage and retrieval means 16 comprises a local data modem 58 operatively coupled between the image scanning and digitizing means 14 through the transmission connectors 44 and bi-directional high speed communication link 25, and a selector or multiplexer 60. A format convertor 62 is operatively coupled between the alternate digitized image source(s) 24 such as CAT 64, MRI 66 and/or video 68 and control computer 70 which is, in turn, coupled to a control console 72 including a visual display and input means such as a keyboard. The local data mode 58 is also coupled to the hard disk (H/D) of the control computer 70 through a conductor 71. The other components of the image data storage and retrieval means 16 are coupled to the control computer 70 through a plurality of conductors each indicated as 73. A CD write drive 74 is operatively coupled between the multiplexer or selector 60 and an auto disk storage/retrieve mechanism 76 which is, in turn, operatively coupled to a CD library storage 78, a manual load/purge box 80 and a plurality of data retrieval and transmission channels each indicated as 81. Each data retrieval and transmission channel 81 comprises a CD reader drive 82 operatively coupled through a corresponding data interface 84 to a corresponding transmission connector 86. In addition, one of the CD reader drives 82 is operatively coupled through a selector switch 88 to an optional CD write/RAM card drive 90 configured to manually receive a compact disk 48 or RAM card.

As shown in FIG. 4, the CD library storage 78 comprises at least one cabinet 200 to operatively house 800 compact disks 48 arranged or four shelves each indicated as 202 and the auto disk storage/retrieval mechanism 76 which comprises a CD coupler 204 to engage and grasp a selected compact disk 48 and move horizontally on a support member 206 that moves vertically on a pair of end support members each indicated as 208. An access door 210 permits movement of compact disks 48 to and from the cabinet 200. However, in normal operation, "old" patient data is removed by writing collected image data to a single compact disk 48 through the CD write/RAM card drive 90 thus freeing internally disposed compact disks 48 for new data. The CD write/RAM card drive 90 may also be used to collect a patient's image data on a single compact disk 48 for use in the operating room's display terminal. This obviates the need for a high speed internal hospital local area network.

The computer associated with the CD robotic arm and drive mechanism performs ordinary library maintenance functions such as retrieval of outdated files, access statistics, entry of access validation codes, and so forth. This computer subsystem also handles data communication interface functions.

Internal to the environmentally controlled cabinet 200 are a plurality of playback mechanisms (field expandable to six) which are automatically controlled by the accessing physicians via the coupled communications system. Yet another CD-ROM write drive can record new data from the image scanning and digitizing means 14 or perform library functions such as consolidation of a patient's data from several compact disks 48 to a single patient-dedicated compact disk 48.

The internal computer maintains a file log of which compact disks 48 are empty and where each patient's image data is stored by disk number and track on a disk location. When the image scanning and digitizing means 14 requests to down-load data, the auto disk storage/retrieval mechanism 76, of the image data storage and retrieval means 16 retrieves the "current" compact disk 48 which is being written with data (if not already loaded), then loads the compact disk 48 into the CD write drive 74, and signals to the image scanning and digitizing means 14 to transmit. Image data is then recorded with a typical record time of 4 minutes for a full-size, high density image.

Once the robotic arm has delivered the compact disk 48 to the CD write drive 74, the robotic arm is free to access and place other compact disks 48 onto CD reader drive 82 as commanded by its communications interface. The robotic arm can find and place a disk 48 into the appropriate CD reader 82 in approximately 10 seconds. Thus, there is minimal waiting time for disk access unless all CD readers drives 82 are in use.

As shown in FIG. 3, data is received through the input transmission connector 44 to the CD write drive 74 through the selector switch 60. Alternately, other image data from other sources such as CAT scanners 64 or MRI medical equipment 66 may be fed through the format convertor 62 for storage on a compact disk 48. If the other image sources are written to CD write drive 74, file identification data must be supplied to the format convertor 62 from the control computer 70.

The image file data received from the image scanning and digitizing means 14 is directly written to free space on a compact disk 48 in the CD write drive 74. No other data compression or special formatting is required as the image scanning and digitizing means 14 has performed these functions. As new image data is received from the image scanning and digitizing means 14 or another image source 24, the image data is sequentially appended to the last file on the compact disk 48 currently being written to. Thus, no attempt is made to organize a single patient's image files onto a single compact disk 48. However, each file received is logged into the control computer 70 through the conductor 71. Therefore, the control computer 70 always knows what disk location in the CD library storage 78 contains any specified file. Once a compact disk 48 is filled with image data, the auto disk storage/retrieve mechanism 76 removes the compact disk 48 from the CD write drive 74 and stores the compact disk 48 in an empty location in the CD library storage 78.

The plurality of data retrieval and transmission channels 81 service the data requests from subscribers. As previously indicated, a single data retrieval and transmission channel 81 includes the select switch 88 to direct image file data to the optional CD write/RAM card drive 90. By this means, all image data for an individual patient may be collected on one or more selected compact disks 48 for archiving or other use. However, normally, the control computer 70 will automatically remove old image data by removing the compact disk 48 from the CD library storage 78 and placing the compact disk 48 in the manual load/purge box 80. The removal age and exceptions information are selected by the system operator from the control console 72.

The control console 72 is also used to enter and maintain subscriber access identification codes in an "authorization file". This updated user authorization file data is sent through a transmission connector 92 to the telecommunications means 18 internal computer memory accessed by the control computer 70 as needed to accept or reject subscriber data link access requests. The user authorization file normally residing in the telecommunications means 18 may be remotely updated by authorized persons.

The number of data retrieval and transmission channels 81 depends on intended subscriber demand. The image data storage and retrieval means 16 is modular and may be upgraded as demand increases. Each data interface 84 operates cooperatively with the telecommunications means 18 to send only as much information as the telecommunications means 18 can compress and transmit to a remote visual display terminal 20 of a requesting subscriber in a given time interval. Thus, the interface is an asynchronous block-buffered type.

Since the entire system 10 is designed to provide easy and quick access to a patient's medical images, it is vital that these images be transmitted to a variety of locations in a timely and cost effective manner and further data compression is imperative. The telephone network is still the most commonly available network but has a severe data rate limitation of about 1200 bytes per second (9600 baud). While other high speed telecommunication channels such as time-shared cable, satellite link may eventually become commonly available, for the immediately forseeable future, the "phone" network must be used if system 10 is to be practical today.

Figure 5:
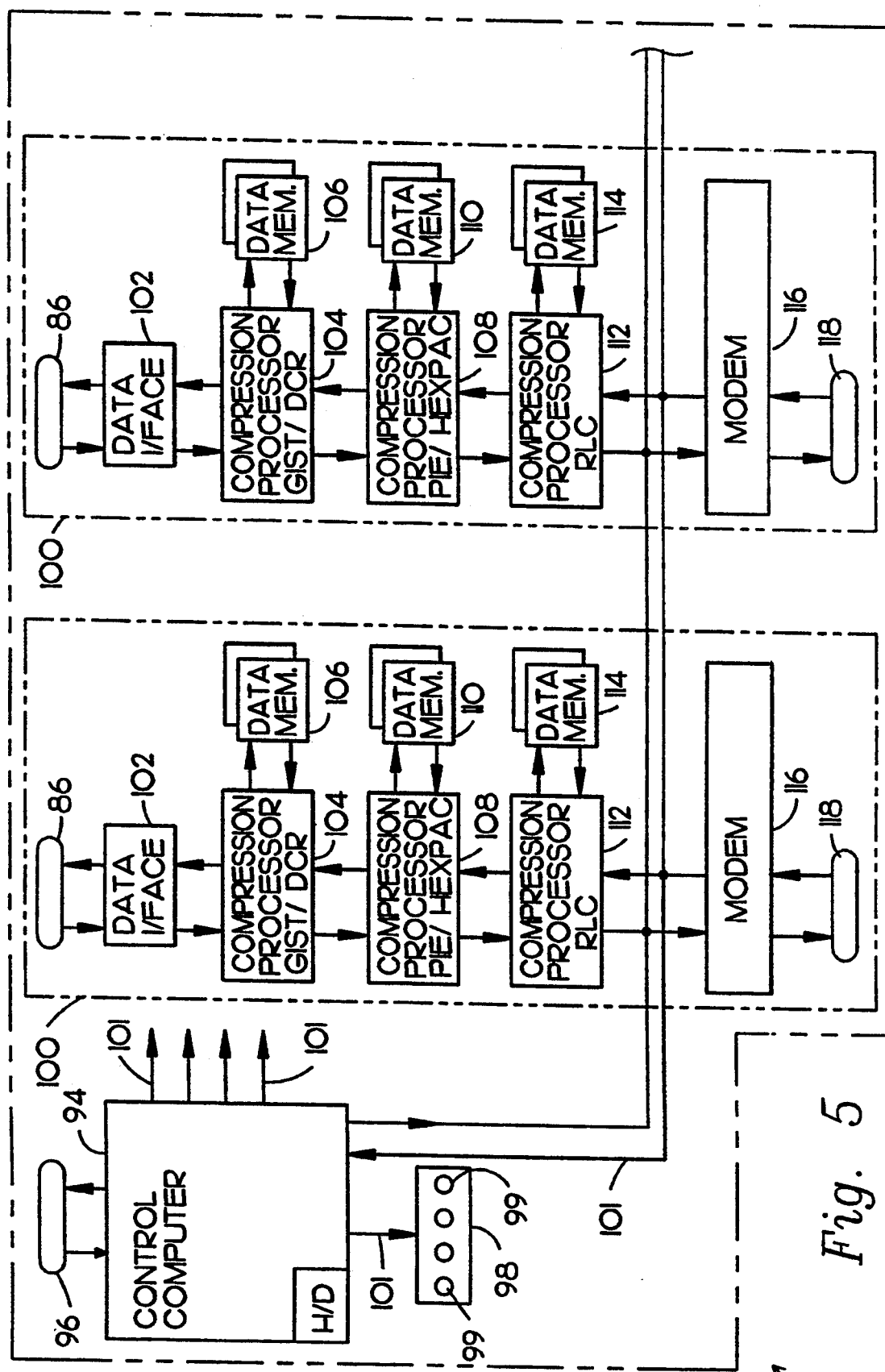
FIG. 5 is a functional block diagram of the telecommunication means.

As noted earlier, a typical medical image may be stored as 119 megabytes of data. At 1200 bytes per second, it could take 27 hours to completely transmit the already compressed medical image data. This is obviously unacceptable. To overcome this obstacle, the telecommunications means 18 as shown in FIG. 5 utilizes five distinct data handling technologies to achieve useful data image transmission in less than one minute:

(1) Guided Image Selection and Transmission or GIST depends upon interactive use by the physician to identify what portions of an image are needed for enhancement or better resolution. Thus the data actually transmitted to the subscriber's visual display terminal 20 is guided by the subscriber observing the image. In particular, once the user has an image displayed on his or her visual display terminal 20, the user may outline a specific region of interest such as a lesion or tumorous growth for more detailed study. The operator may select this region using a "mouse" or light pen or similar well-known computer display terminal peripheral device. Having selected this region, the visual display terminal 20 will display the more detailed pixel data be sent on this region. The telecommunications means 18 will continue to send further precision data until the natural resolution limits of the display are reached or all available data is sent and received. This process of expanding an image region is known as "zooming" in computer-aided design systems. The novel feature here is that the image is further refined in resolution when "zoomed". The means for doing this and knowing when to "stop" further pixel transmission is defined by the PIE and DCR technology described hereinafter, (2) Progressive Image Enhancement or PIE utilizes the transmission time from the instant a first "crude" image is presented to the subscriber to the present time of observation to progressively enhance the quality of the presented image. The longer the user observes a selected image, the "better" the image becomes in the sense of pixel resolution and quantity of gray levels. In the preferred embodiment, hexagonal pixel groups are first transmitted using the HexPac pattern compression technology described hereinafter. Once a full terminal screen display has been made composed of these hexagonal patterns, then the telecommunications means 18 transmits more precise pixel detail. First all pixels located on the periphery of each hexagonal group are updated with their exact gray level values and thereafter, all inner pixels are similarly updated. If the display terminal's resolution is less than the 1000 dots per inch of the source image data, then pixel groups are sent, such as a square of four pixels, which match the display resolution and "zoom" expansion selected. This display matching technique is further defined hereinafter as DCR, (3) Display Compatible Resolution or DCR transmits information about the user's terminal 20 back to the telecommunications means 18. Only data with a resolution compatible with that terminal 20 will be sent. Any excess data-link connect time can be used to send other image data which is likely to be requested or has been pre-specified to be sent.

(4) An image pattern compression method comprising a Hexagonal Pattern Classification or HexPac exploits the two dimensional nature of images. The data received by telecommunications means 18 is first uncompressed and placed into a multi-scanline digital buffer. This image data is then divided up into hexagonal cells and matched against predefined patterns. Many fewer bits of data can be used to represent these predefined patterns, thus substantially compressing the image data for phone-line transmission. The pixels of these hexagonal patterns may easily be "refined" by the PIE technology described earlier. If the DCR subsystem determines that the user terminal has a pixel area of, say, 1500 by 1000 dots, then the HexPac technology recreates a new super pixel which is the average gray level of all actual pixels within that super pixel area. This immediately reduces the quantity of pixels to be sent (to only 1500 by 1000 pixels). Without further data compression, this quantity of data would still require about 26 minutes of data transmission time at 9600 baud, the highest available phone network data rate.

(5) Run length coding or RLC permits data to be compressed by specifying how many pixels have the same gray level in a sequence or "run length" of scanning. The image data sent by a CD reader drive 82 to telecommunications means 18 is compressed with run-length coding but is nearly loss-less in the duplication of the original film data. To substantially reduce the quantity of data needed to send an acceptable medical image to a remote user terminal 20 over the data-rate limited phone-line modem, a "lossy" compression is used. Since the PIE and DCR techniques described earlier will eventually provide any degree of diagnostic image integrity desired, it is believed acceptable to initially transmit a "lossy" image provided it gives adequate resolution for the user to begin the analysis and guided image selection. Many fewer bits can describe this "run" of similar gray levels thus compressing the amount of data sent. This technique is well known and often used in facsimile transmission. A one dimensional RLC is incorporated in the preferred embodiment but since HexPac elements are being coded, it can be considered more accurately a quasi two dimensional RLC compression.

FIG. 5 is a functional block diagram of the telecommunications means 18 including a control computer 94 operatively coupled to the image data storage and retrieval means 16 through a transmission connector 96. The various components of the telecommunications means 18 including a status panel 98 with a plurality of system indicators each indicated as 99 and a plurality of data compression channels each generally indicated as 100 coupled to the control computer 94 by a plurality of conductors each indicated as 101.

Each data compression channel 100 comprises a transmission connector 86, a communications data interface 102, a first compression processor or means 104 including logic means to generate the GIST and DCR data compressions and corresponding first data memory 106, a second compression processor or means 108 including logic means to generate the PIE and HEXPAC data compressions and corresponding second data memory 110 and a third compression processor or means 112 including logic means to generate the RLC data compression and corresponding third data memory 114, a corresponding modem 116 and a transmission connector 118.

The control computer 94 coordinates or controls data flow to and from the plurality of data compression channels 100 through the transmission connectors 86 and 118 respectively. Validated subscriber image data requests are transmitted to the image data storage and retrieval means 16 which searches the image library file 78 for availability of the requested compact disk 48. If available, the image data storage and retrieval means 16 loads the appropriate disk 48 from CD library storage 78 into a CD reader drive 82 and informs telecommunications means 18 through the transmission connector 96 to the control computer 94 that a specific data interface 84 has data available to be transmitted through the corresponding transmission connectors 86. Once a subscriber transaction has been turned over to a specific data retrieval and transmission channel 81, the data compression channel 100 receives the data therefrom unless commanded to stop by a feedback control line. The data interface 102 is used to inform the CD reader drive 82 as to what portion of the image is requested by the first compression means 104. Generally, the complete image is first requested. Thus the CD reader drive 82 is requested to read the image data from the start.

The data is temporarily stored in the first data memory 106. Here the pixel data is first expanded from the RLC code into uncompressed pixel data. This is only done on a relatively few number of scan lines—about one tenth of an inch height of original image data. This uncompressed data is then remapped by the first compression means 104 into "larger" pixels whose average intensity is the average of all combined pixels compatible with the display resolution receiving remote visual display terminal 20. This "super pixel" data is then fed to the second data memory 110. The super pixel data in memory 110 is then processed by the second compression means 108. Initially, the lowest resolution image will be transmitted to rapidly form a useful remote image on the requesting remote visual display terminal 20 through a communications network 21. This will be done by combining super pixels in the second data memory 110 into hexagonal patterns which approximate the group of super pixels. These HexPac data packets are then sent to the third data memory 114. There the HexPac data packets are further compressed by the third compression means 112. These packets of run-length coded HexPac data packets are then transmitted through the corresponding modem 116 and transmission connector 118 over the selected communications network 21. The modem 116 includes state of the art error control techniques such as block retransmission when a remote error has been detected. Thus, data transmission is essentially error-free as needed for compressed data handling.

The control computer 94 includes circuitry means to monitor the activity of each data channel. The identification of each subscriber is logged along with the total connect time for billing purposes. Thus the control computer 94 generally coordinates the plurality of communication links and their connections to the particular data retrieval and transmission channel 81 within the image data storage and retrieval means 16 as well as granting access and performing connection accounting tasks. The status panel 98, connected to the control computer 94 is used to aide in system debug and indicate operation of the data compression channels 100. The status panel 98 would not normally be used by hospital personnel but by system service technicians.

The control computer 94 also has a permanent memory such as a hard disk to record subscriber usage data and internally sensed hardware problems. This data may be downloaded on any of the transmission connectors 118 when a correct authorization code has been received. Thus, the servicing company can acquire subscriber usage information remotely for billing purposes and system diagnostic purposes.

The preferred embodiment of the telecommunications means 18 uses modular communication channel hardware. Thus, the module may be customized to function with any type of communication channel such as satellite links, cable networks or a local area network such as Ethernet or ISDN services.

It is important to note that all communications is bidirectional so that if, say, a remote visual display terminal 20 should become temporarily "overloaded" with image data due to decompression processing delays or due to a detected data error, then, the remote visual display terminal 20 may request that data transmission be stopped or a block of data be repeated until it is received correctly.

Figure 7:
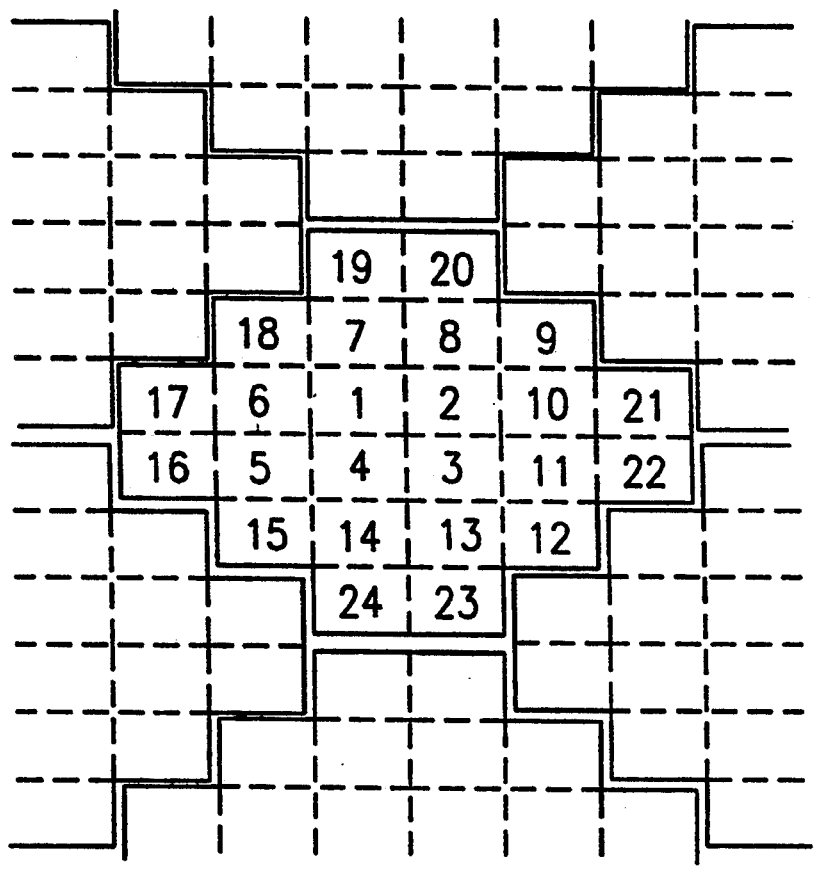
FIG. 7 depicts the hexagonal pattern of the hexagonal compression method.

FIG. 7 graphically shows a hexagonal group of the hexagonal compression method comprising a group of square image pixels partitioned into a hexagonal group. The pixels are numbered for convenience of reference from the inside to the outside in a clock-wise manner. Each hexagonal group or packet comprises 24 super pixels as earlier described but other numbers are possible. It is assumed that each pixel is gray level coded using 2 bytes of data. Thus, the hexagonal group requires (24×2) 48 bytes of data to fully represent the 24 super pixels comprising the image pattern at the user terminal 20.

Figure 8:
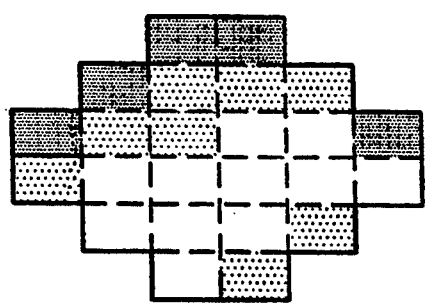
FIG. 8 depicts an actual hexagonal pattern from an X-ray film.
Figure 9:
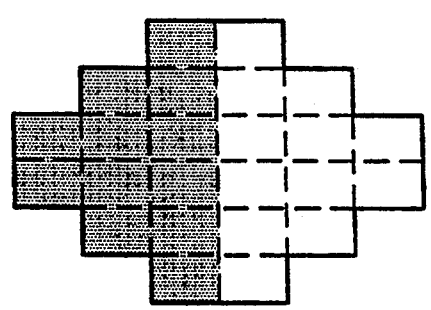
FIG. 9 depicts the selected predetermined hexagonal pattern most closely corresponding to the actual hexagonal pattern shown in FIG. 8.
Figure 10:
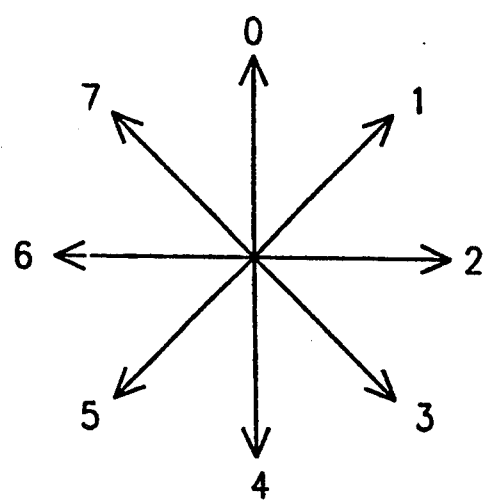
FIG. 10 graphically represents the predetermined rotational orientations for the predetermined hexagonal patterns.

FIG. 8 shows a typical pattern as may occur in a region of an X-ray film 12. The method predefines a group of likely patterns, one of which is represented as a "best" match as in FIG. 9 with the actual pattern in FIG. 8. As shown in FIGS. 14A through 14H, there are 8 possible predetermined representative gray level patterns represented by 3 bits. These patterns are specifically selected to be essentially uncorrelated with each other even if rotated relative to each other. As shown in FIG. 10, these patterns may be rotated through 8 equal angles (another 3 bits of data) to best match the actual pattern. Rotation angle "1" is shown in FIG. 10 as the best match for the given example. Thus far, six bits have been used to approximate the actual pattern of FIG. 8. As shown in FIGS. 14A through 14H, each fictitious pattern includes a dark and light regions and origin. Although FIG. 11 discloses a straight gray level slope corresponding to the pattern shown in FIG. 14A, the gray level slope will vary with the fictitious pattern. For example, the gray level slope of the fictitious pattern shown in FIG. 14D would closely approximate a V shape.

Figure 11:
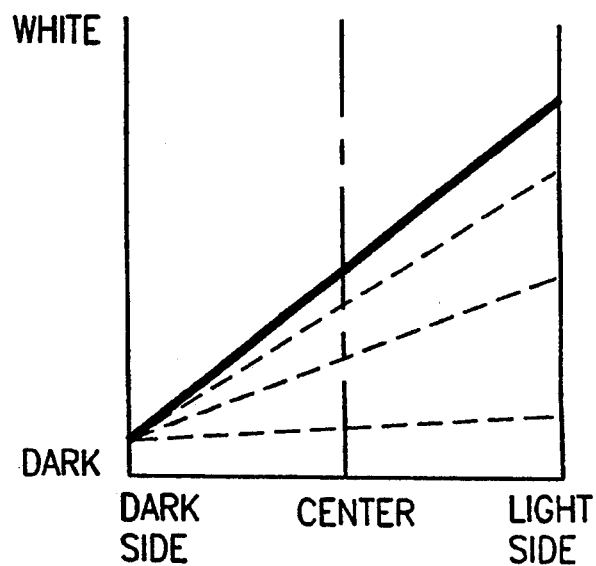
FIG. 11 graphically depicts a selected gray level slope of the selected predetermined hexagonal pattern of FIG. 9.

FIG. 11 shows how the gray level slope may be discretely selected to best match the slope of the actual pattern. Two bits are used to approximate this slope.

Figure 12:
FIG. 12 depicts a single pixel from the predetermined hexagonal pattern.

FIG. 12 shows that one particular pixel, such as the darkest pixel, has been selected to be fairly precisely gray level represented by means of 8 bits (256 gray levels).

Figure 13:
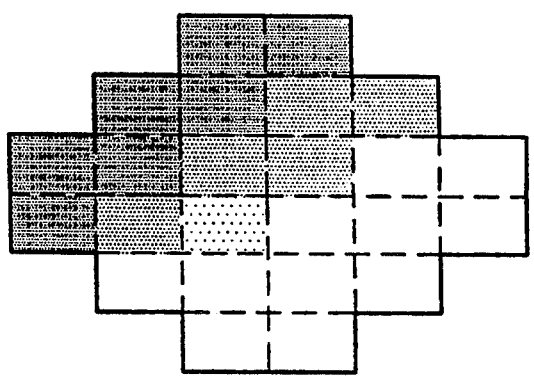
FIG. 13 depicts a hexagonal pattern reconstructed by a remote display terminal means corresponding to the actual hexagonal pattern shown in FIG. 8.

The total bits required to approximate the actual pattern is 16 or two bytes. FIG. 13 shows how this fictitious or reconstructed pattern may be reproduced at the user terminal 20 when decoded.

In this example, only two bytes were required to represent "adequately" an original 48 bytes of image data. Thus, a 24 to 1 compression ratio has been achieved. Further, run-length encoding (RLC) may be used on these HexPac groups to further reduce redundant spans of white and black. It is estimated that the combined compression ratio of HexPac and RLC on the super-pixel image is about 36 to 1 for this particular set of parameters. This combined compression technology reduces data transmission time (at 9600 baud) to approximately 43 seconds for an initial useful medical image.

For medical images, further enhancements through the PIE compression should favor the elimination of artificial lining between hexagonal patterns first. As the user continues to view the same image, then the PIE compression will progressively improve the gray level integrity by updating all number 24 pixels to 8 bits of gray level resolution and updating all number 23 pixels to 8 bits of gray level and so forth for all remaining pixels in descending order. This process takes about 10 minutes at 9600 baud to update all peripheral hexagonal pixels and about 20 minutes total for all pixels.

If the user continues to observe or request further image resolution, the telecommunication means 20 causes each pixel gray level to be updated by one additional bit in descending order again until the full 16 bits of gray level is received and stored at the terminal 20 for each super pixel. Each doubling of gray level resolution takes between 1 and 2.6 minutes at 9600 baud depending on the run length statistics of the gray levels.

Figure 6:
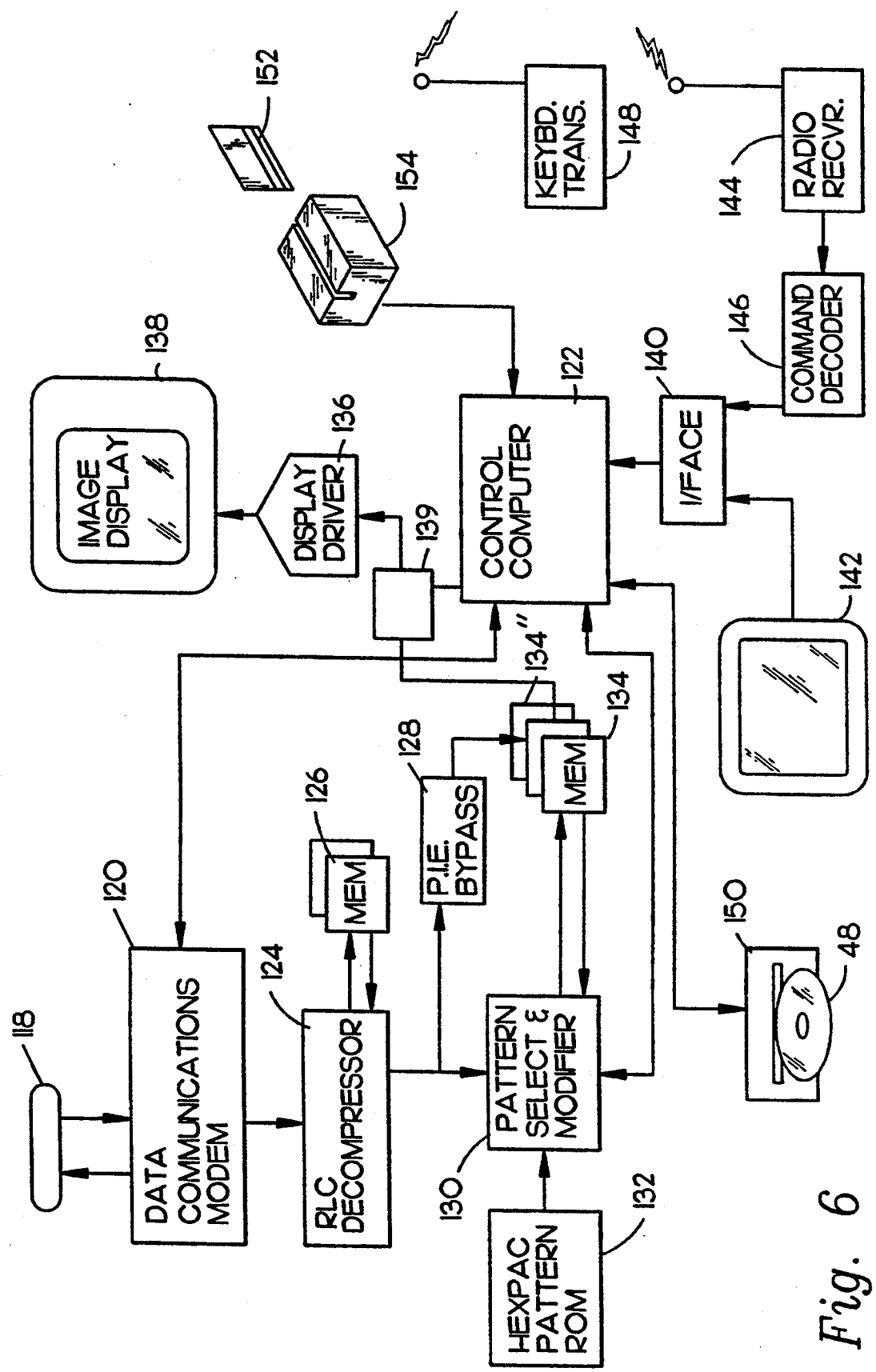
FIG. 6 is a functional block diagram of the remote display terminal means.

FIG. 6 is a functional block diagram of a remote visual display terminal 20 to be operatively coupled to one of the data compression channels 100 of the telecommunication means 18 by a communications network 21 and a transmission connector 118. The visual display terminal 20 comprises a data communications modem 120 operatively coupled to a control computer 122 and RLC decompression means 124. The RLC decompression means 124 is, in turn, operatively coupled to a memory 126, a PIE bypass 128 and a pattern select and modifier 130 which is operatively coupled to a HexPac pattern ROM 132 and the control computer 122. A memory 134 is operatively coupled between the PIE bypass 128 and pattern selector and modifier 130 and a display drive 136 which is operatively coupled to an image display 138. In addition, an image enhancing processor means 139 including circuitry to generate edge contrast enhancement, gray level contrast enhancement by means of gray level region expansion or differential gray level tracking and gray level enhancement or other state of the art image enhancement method well known to those skilled in the art. The control computer 122 is operatively coupled to an interface 140 to a first control or selector means 142 and a second control or selector means including a radio receiver 144 and signal command decoder 146 for use with portable keyboard transmitter 148. In addition, an optional CD read/write drive 150 may be provided for use with a compact disk 48.

The modem 120 has built-in compatible error correction technology to communicate with corresponding transmitting data compression channel 100. After the user has selected the image data storage and retrieval means 16 and validated authority by swiping through an identification magnetic card 152 or otherwise through a magnetic card reader 154 entered an assigned security code, the operator may select a patient and one or more image files presented to him on the display screen 138. Selection is accomplished by a touch-screen overlay on the first control or selector means 142 or by the keyboard transmitter 148 of the second control or selector means.

Once one or more images have been selected by the user, the modem 120 writes image data to the temporary memory 126 which is actively accessed by the RLC decompression means 124. This decompressed data describes the HexPac patterns or packets as stripes of the image running, for example, sequentially from left to right. These Hexpac pattern specifications, typically 2 data bytes or 16 bits are then routed to a pattern selection processor 130 which accesses the predefined patterns from Read-Only Memory device 132. Each pattern is then rotated and gray-level modified by processor 130 according to the HexPac 16 bit pattern specification received from the RLC decompression means 124. Each modified pattern is then written to a graphics display memory circuit 134. As the graphics display memory circuit 134, develops the pattern data, the display driver 136 and image display 138 show the image on the screen as it is received. In this manner, the entire "first pass" medical image is painted on the image display 138 screen.

If the user makes no further intervention, then once the image is fully displayed on this "first pass", then the progressive image enhancement technology requests pixel enhancement data. This enhancement data bypasses pattern selector and modifier 130 and is routed through the PIE bypass 128. In the PIE bypass 128, the enhanced pixel information is directed to the correct graphic memory locations in the graphics display means circuit 134'. Thus, the display driver 136 and image display 138 are continually resolution enhanced.

If the image is fully enhanced to the limits set by the DCR in the control computer 122, the image storage and retrieval means 16 is directed by the control computer 122 to begin sending new image data on the next selected image and begin storing this image data in a second graphics display memory circuit 134". This second data memory 134" can hold one or more images and may be selected immediately by the user when he is finished inspecting an earlier image. The user may further direct by touch screen command 142 that these be stored in the computer's hard disk or archived by the optional CD read/write drive 150.

The user may at any time select a portion of the displayed image for further expansion by enabling or selecting the Guided Image Selection & Transmission (GIST) circuitry in the control computer 122 or image enhancement through the image enhancing processor means 139. This may be accomplished either by touch screen control means 142 or the second remote control means 144/146/148. This remote keyboard and transmitter unit 144/146/148 duplicates the on-display simulated push-buttons of the touch screen control means 142. Coded command signals sent by 148 are received by radio receiver 144 and decoded by 146. These commands are then accepted by control computer 122 as though they were normal keyboard commands.

The user may terminate a session with the image data storage and retrieval means 16 at any time by selection of stop and escape command. While a printer is not shown in this description, it can be an optional addition to terminal 20.

In summary, the image data storage and retrieval means 16 selects the first image and writes that data to a temporary memory buffer in the telecommunication means 18. Information about the subscriber's terminal is uploaded to the telecommunications means 18 so that the Display Compatible Resolution (DCR) logic circuitry knows when to stop sending added data for the requested first image. A special interactive compression computer then compresses this first image data using the HexPac circuitry and sends that data over the data link modem to the subscriber terminal 20. Error detection and correction methods will generally be used in this communications link protocol.

Once a first "crude" image is sent to the subscriber visual display terminal 20, then the Progressive Image Enhancement (PIE) circuitry begins to send additional data to further refine the resolution of each hexagonal pixel region. If no further guidance is given by the subscriber, the PIE will continue to refine the picture's resolution until its natural limit is sent for the terminal 20. Thereafter, the PIE will begin sending image data from the second specified film and loading it into yet another memory buffer. Thus, the data link connection is always transmitting useful data even though the subscriber may only be analyzing one image for some time.

However, should the user desire to zoom in on a particular region of an image, he or she may define that region desired on the terminal 20 by the Guided Image Selection & Transmission (GIST) to expand the visual display accordingly. The DCR will recognize the requirement for additional resolution and command the PIE to begin transmitting additional pixel information until such time as the DCR informs it that once again the natural display resolution limit has been reached.

The following image enhancement means present in the instant invention: edge contrast enhancement, gray level constrast enhancement by means of gray level region expansion or differential gray level tracking and gray level enhancement and may be accomplished by the image enhancing processor means 139 in the visual display terminals 20.

The human eye cannot reliably discern gray level differences less than approximately 2%. Yet, significant tissue density information causes X-ray gray level differences in this range and below. The enhancement technologies above will cause these tissue density differences to be magnified thus revealing hitherto unseen image data.

To ensure ease of use, the following features are incorporated: touch-screen selection of commands, magnetic card identification of the subscriber or user, icon based menus or selection buttons on the CRT display and split image display screen overlays.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

We claim:

1. An image storage, retrieval and transmission system comprising
    means forming an initial digitized image,
    computer means storing said digitized image,
    telecommunication means linking said computer means to a remote visual display terminal, said telecommunication means comprising compression means including logic means to
        generate a plurality of regions collectively representative of said image, each said region comprising a plurality of two dimensional, non-overlapping, symmetrically disposed supper pixels and to
        compare each said region with a plurality of fictitious patterns, each said pattern having a dark region, a light region and a predetermined point of origin, and thereby to determine which of said plurality of fictitious patterns most closely correlates with said region and to generate a compressed digitized representation corresponding to said selected fictitious pattern, and
    wherein said remote visual display terminal includes means to generate and display an image corresponding to said fictitious pattern.

2. A system of claim 1 wherein said fictitious patterns are selected to be essentially uncorrelated with each other when rotated relative to each other.

3. A system of claim 2 further including logic means to select a fictitious pattern having a gray level most closely correlated with a gray level of a said super pixel.

4. The system of claim 1 wherein said means forming an initial digitized image comprises a format converter having a digital video signal as an input.

5. The system of claim 1 wherein said means forming an initial digitized image comprises a medical X-ray film and an image scanner.

6. A system of claim 1 wherein said compression means further includes logic means to determine which of said plurality of fictitious patterns most closely correlates with said region and to generate a compressed digitized representation corresponding to said selected fictitious pattern, and wherein said remote visual display terminal includes means to generate and display an image corresponding to said fictitious pattern and means to rotate a said selected pattern to that one of a plurality of predetermined rotational orientations that most closely approximates said super pixel.

7. A system of claim 1 wherein said remote visual display terminal includes
    means to generate and display an image closely correlated to said actual super pixels in response to receiving said compressed digitized image data corresponding to said selected fictitious patterns and
    logic means to generate a set of predetermined representative gray levels wherein each said gray level is that one most closely correlating with the gray levels of said actual super pixel.

8. A system of claim 7 wherein said terminal means further comprises logic means to rotate a said selected pattern to that one of a plurality of predetermined rotational orientations that most closely approximates said actual super pixel.

9. A system of claim 1 wherein said telecommunication means further includes means to compress and transmit to said remote terminal digitized image data specific to a selected sub-image and wherein said remote terminal further comprises means to provide a visual display of said selected sub-image.

10. A system of claim 9 wherein said compression means further includes progressive image enhancement means transmitting, subsequent to a display of a said selected sub-image, data representative of exact gray levels of those super pixels located on a periphery of each region within said selected sub-image and thereafter transmitting similar data for those super pixels interior to each said region, whereby the resolution of said displayed sub-image increases with time.

11. A system of claim 10 wherein said terminal has a resolution limit, wherein said terminal comprises means to communicate said resolution limit to said telecommunication means, and wherein said telecommunication means sends no additional data if the resolution of said displayed sub-image is equal to said resolution limit.

12. A system of claim 1 wherein said compression means further includes run length compression of said fictitious patterns.

13. A system of claim 1 wherein said remote visual display terminal further includes image enhancement means to enhance a displayed image.

14. A system of claim 13 wherein said image enhancement means includes logic means to enhance an edge contrast of a displayed image.

15. A system of claim 13 wherein said image enhancement means includes logic means to enhance gray level contrast by means of gray level region expansion.

16. A system of claim 13 wherein said image enhancement means includes logic means for differential gray level tracking and gray level enhancement.

17. A system of claim 1 wherein said telecommunication means further comprises means to enhance the gray scale of a said image,
    means to transmit to said terminal a first data block usable to reconstruct a said image without said enhancement, and
    means to transmit to said terminal a second data block usable to reconstruct said image with a said enhanced gray scale.

18. A system of claim 1 wherein said compression means further includes progressive image enhancement means transmitting, subsequent to a display of a said image, data representative of exact gray levels of those super pixels located on a periphery of each region within said image and thereafter transmitting similar data for those super pixels interior to each said region, whereby the resolution of said displayed image increases with time.

19. A system of claim 18 wherein said terminal has a resolution limit, wherein said terminal comprises means to communicate said resolution limit to said telecommunication means, and wherein said telecommunication means sends no additional data if the resolution of said displayed image is equal to said resolution limit.

20. A method of acquiring, storing, retrieving and displaying an image comprising the steps of
    a) acquiring a said image having a first resolution, and translating said image to a predetermined digital format, b) storing said digitized image in a computer memory at a first location, c) requesting, from a user-operated terminal having a first resolution limit and located at a second location, a said digitized image, d) creating from said digitized image, at said first location a patterned and compressed representation thereof by means of a hexagonal pattern classification algorithm comprising the steps of d1) generating a plurality of regions collectively representative of said image, each said region comprising a plurality of two dimensional, non-overlapping, symmetrically disposed super pixels, d2) comparing each said region with a plurality of fictitious patterns, each said pattern having a dark region, a light region and a predetermined point of origin, d3) selecting that one of said plurality of fictitious patterns that most closely correlates with said each said region, e) transmitting from said first location to said terminal a first portion of said stored patterned representation, f) reconstructing, at said terminal, by means of a second algorithm, from said first portion of said patterned representation, a first displayable representation of said diagnostic image, said first displayable representation having a second resolution less than said first resolution, and g) displaying said displayable representation at said terminal.

21. The method of claim 20 further comprising the steps of:

h) transmitting from said first location to said terminal an additional portion of said patterned representation, i) reconstructing, at said terminal, by means of a third algorithm, from said additional portion of said patterned representation, an improved displayable representation of said image, said improved displayable representation having a third resolution greater than said second resolution, j) repeating steps g), h) and i), thereby progressively increasing the resolution of said displayed representation until said displayed resolution attains the lesser of said first resolution of said image or said predetermined resolution limit of said terminal.

22. A method of claim 21 further comprising an additional step before step h) of defining, by means of a user-operated computer-interactive device, a sub-image of said visual representation, and wherein said subsequent reconstructions in step j) are directed at reconstruction only of said sub-image.

* * * * *

UNITED STATES PATENT AND TRADEMARK OFFICE
CERTIFICATE OF CORRECTION

PATENT NO. : 5,384,643
DATED : 1/24/95
INVENTOR(S) : Inga et al

It is certified that error appears in the above-identified that said Letters Patent is hereby corrected as shown below:

In claim 1, at column 19, line 19, after "symmetrically disposed" the word "supper" should be replaced with --super--.

Signed and Sealed this

Ninth Day of May, 1995

BRUCE LEHMAN

*Attest:*

*Attesting Officer*        *Commissioner of Patents and Trademarks*